United States Patent [19]

Fizet

[11] Patent Number: 4,939,276
[45] Date of Patent: Jul. 3, 1990

[54] CONCENTRATION OF NATURAL INGREDIENTS FROM NATURAL MATERIALS

[75] Inventor: Christian Fizet, Zimmersheim, France

[73] Assignee: Hoffmann-La Roche Inc., Nutley, N.J.

[21] Appl. No.: 270,604

[22] Filed: Nov. 14, 1988

[30] Foreign Application Priority Data

Nov. 19, 1987 [CH] Switzerland .......................... 4509/87

[51] Int. Cl.⁵ ...................... C07D 311/72; C07J 9/00
[52] U.S. Cl. .................................... 549/413; 552/545
[58] Field of Search .................... 260/397.25; 549/413

[56] References Cited

U.S. PATENT DOCUMENTS

| | | | |
|---|---|---|---|
| 3,108,120 | 10/1963 | Brown et al. | 549/413 |
| 3,332,969 | 7/1967 | Hutt, Jr. | 260/397.25 |
| 3,983,147 | 9/1976 | Senda et al. | 260/397.25 |
| 4,594,437 | 6/1986 | Sampathkumar | 549/413 |

FOREIGN PATENT DOCUMENTS 2182229 12/1973 France .
114628 1/1983 Japan .

*Primary Examiner*—Nicky Chan
*Attorney, Agent, or Firm*—George M. Gould; Bernard S. Leon; William H. Epstein

[57] ABSTRACT

A novel process for the concentration of natural tocopherols and/or steroids in materials derived from natural sources by treating this material with calcium hydroxide in the presence of water in an inert water-miscible organic solvent and subsequently separating from this material the thus-formed calcium salts.

13 Claims, No Drawings

CONCENTRATION OF NATURAL INGREDIENTS FROM NATURAL MATERIALS

SUMMARY OF THE INVENTION

In accordance with this invention, it has been discovered that the naturally derived materials which contain naturally occurring vitamins such as tocopherols and pharmaceutically active steroids can be concentrated by treating the natural derived material with calcium hydroxide in the presence of a solvent medium containing water and a inert water miscible organic solvent to form calcium salts of natural occurring fatty acids. These calcium salts are precipitated and removed. After such treatment and removal of the calcium salts, the material in the liquid phase contains the natural tocopherols and/or steroids in a far more concentrated amount from that present in the natural derived material used as the starting material.

In this manner, natural tocopherols and steroids can be recovered from materials derived from natural sources. This process provides a simple and economic means for commercially producing tocopherols or steroids through isolation from natural materials, particularly vegetable oils.

DETAILED DESCRIPTION

The present invention is concerned with a novel process for the concentration of natural tocopherols and/or of steroids present in natural sources. The production of natural tocopherols from natural sources such as vegetable materials has become increasingly important and many different processes for this purpose are already known. The production of certain steroids from such sources has also become increasingly important.

The term natural tocopherols embraces in the scope of the present invention not only the $\alpha$-, $\beta$-, $\gamma$- and $\delta$-tocopherols, but also the corresponding tocotrienols, tocodienols and tocoenols.

In carrying out this invention any of the known naturally derived materials which contain tocopherols and/or steroids can be utilized as the starting materials. Generally these materials also contain fatty acids both as free fatty acids or salts, and as esters with glycerol (glycerides). These fatty acids are those which are normally present in natural oils and fats. The starting material is also generally present in liquid form. By the process of this invention, treatment of the starting material with calcium hydroxide in a solvent medium containing water and a water miscible solvent produces the calcium salts of these fatty acids which can be precipitated from the calcium treated starting material. The precipitate is then removed leaving the tocopherols and/or steroids in a more concentrated form in the remaining naturally derived material. In this manner the tocopherols and/or steroids present in the naturally derived material can be concentrated in the remaining material to a weight percent of at least 2 × their weight percent in the starting material. This weight percent is based upon the total weight of the material. Generally by this procedure the tocopherol and/or steroids are concentrated to a weight percent of from 2 × to 6 × their weight percent in the starting naturally derived material.

As vegetable derived starting materials for the production of natural tocopherols or of certain steroids by the process of this invention, the distillates (vapour-separated fats) obtained in connection with the production of edible oils and fats after the deodorization step are generally preferred for use in this invention. In particular, the residues from the deodorization of the usual edible oils and fats such as e.g. sunflower oil distillates, soya oil distillates, rape oil distillates, cotton seed oil distillates, palm oil distillates etc. are utilized. However, the non-deodorized oils and fats as well as the aforementioned residues, which have already been subjected to a further concentration step, can also be used.

These starting materials generally contain the tocopherols as well as free fatty acids and glycerides of acids normally present-in oils and fats, salts of fatty acids, steroids with the remainder, to some extent, being unidentifiable accompanying substances. The quantitative amount of these substances generally varies very widely depending on the type of starting materials and the manner in which they have been obtained. In the previously mentioned residues of the deodorization, the amount of tocopherols generally is from about 1 to 20 wt.%, with amounts from about 2 to about 15 wt.% being most common. The amount of steroids in said materials is generally from about 4 to about 15 wt.%. This weight % is based upon the total weight of the starting material. The total amount of free fatty acids, glycerides and salts generally amounts to from about 50 to about 85 wt.% and the amount of unidentifiable remainder is from about 5 to about 20 wt.%. In fats and oils which have not yet been deodorized or in residues of the deodorization which have already been concentrated further, these values naturally lie correspondingly lower or higher. These amounts can be determined readily in each case by a person skilled in the art.

Having regard to the relatively small amount of tocopherols or steroids in the starting materials in comparison to the amount of the other compounds, it is desirable first to enrich the tocopherols and/or the steroids content in the starting materials. This enrichment can be effected e.g. by separating the accompanying substances, i.e. especially the free fatty acids and the glycerides. This is effected in accordance with the invention by treating the starting materials containing the substances to be enriched with calcium hydroxide in the presence of water in a water-miscible inert organic solvent and separating the thus-formed calcium salts.

Any conventional water-miscible organic solvent can be used in accordance with this invention. The preferred water-miscible organic solvents for use in this invention are the lower alcohols with 1 to 6 carbon atoms such as e.g. methanol, ethanol, propanol, isopropanol and the like.

By the aforementioned addition of calcium hydroxide the free fatty acids are converted into calcium salts. Since this reaction is carried out in the presence of water, the glyceride esters which are present are, moreover, saponified with the formation of fatty acid calcium salts. The separation of the thus-obtained calcium salts is conveniently effected by removing the water-miscible organic solvent which is used and precipitating these calcium salts with another suitable solvent. As solvents for precipitating the calcium salts thus formed, any conventional water immiscible polar solvent can be used. These polar solvents are suitable for precipitating the fatty acid calcium salts formed during this process. Examples of these polar solvents include methyl or ethyl formate or acetate as well as ketones or nitriles, especially readily volatile representatives thereof such as, for instance, acetone, acetonitrile and the like.

The amount of calcium hydroxide which is used in the process in accordance with the invention is not critical and depends on the amount of fatty acids and glycerides present and can be established readily by a person skilled in the art.

The amount of water which is used in the process, in accordance with this invention, conveniently lies between about 3 and about 15 wt.%, preferably at about 6 to 8 wt.%, based on the weight of solvent medium used.

The treatment of the starting materials with the calcium hydroxide is conveniently effected at a temperature from about 60° C. to about 110° C., preferably at the reflux temperature of the reaction mixture. Depending on the solvent which is used, the treatment must be carried out in certain cases in a pressure vessel (autoclave) in order to ensure that the aforementioned temperatures are attained.

By means of the process of this invention it is possible in a simple manner and in a single step not only to separate fatty acids as well as the glycerides present in the starting material (by simple filtration or centrifugation of the corresponding calcium salts) and at the same time to concentrate the weight percent of the tocopherols and/or steroids present by a factor of at least 2 times, generally, from about 2 to about 6 times depending on the starting material used.

Subsequently, the tocopherols and/or the steroids can be produced from the thus-obtained concentrates in a manner known per se, e.g. by extraction, distillation, crystallization etc.

EXAMPLE 1

A sunflower oil distillate of the following composition is used as the starting material:

|  | Wt. % |
|---|---|
| Tocopherols | 2.5 |
| Fatty acid calcium salts | 25 |
| Fatty acids | 36 |
| Glycerides | 15 |
| Water | 3 |
| Remainder | 18.5 |

100 g of the above distillate are taken up in 750 ml of isopropanol while gassing with argon in a four-necked sulfonation flask fitted with a reflux condenser, thermometer and stirrer. After adding 50 ml of water and 10 g of calcium hydroxide the mixture is stirred at reflux temperature for 6 hours. The solvent is subsequently removed on a rotary evaporator and the residue is taken up in 750 ml of ethyl acetate. The suspension obtained is stirred at room temperature for ½ hour and then cooled to 0° C. The solid is then filtered off under suction and rinsed with 100 ml of ethyl acetate. The filtrate is concentrated completely on a rotary evaporator and there are obtained 22 g of a residue containing 10.8% tocopherols (95% yield).

EXAMPLE 2

A soya oil distillate of the following composition is used as the starting material:

|  | Wt. % |
|---|---|
| Tocopherols | 9 |
| Fatty acid calcium salts | 2 |
| Fatty acids | 39 |
| Glycerides | 32 |
| Water | 1 |
| Remainder | 17 |

100 g of the above distillate are processed while gassing with argon in a four-necked sulfonation flask fitted with a reflux condenser, thermometer and stirrer in a manner analogous to that described in Example 1. There are obtained 26.3 g of a residue containing 31% tocopherols (90% yield).

EXAMPLE 3

A sunflower oil distillate of the following composition is used as the starting material:

|  | Wt. % |
|---|---|
| Tocopherols | 2.4 |
| Fatty acid calcium salts | 20 |
| Fatty acids | 43 |
| Glycerides | 13 |
| Water | 4 |
| Remainder | 17.6 |

100 g of the above distillate are processed while gassing with argon in a four-necked sulfonation flask fitted with a reflux condenser, thermometer and stirrer in a manner analogous to that described in Example 1, with the difference that the residue is taken up in methyl acetate instead of in ethyl acetate. There are obtained 21.5 g of a residue containing 10.6% tocopherols (95% yield).

EXAMPLE 4

A palm oil distillate of the following composition is used as the starting material:

| Tocopherols (tocopherols +1 tocotrienols) | 1.1% |
|---|---|
| Fatty acids | 64% |
| Glycerides | 15% |
| Residue | 19.9% |

100 g of the above material are taken up in 600 ml of isopropanol while gassing with argon in a four-necked sulfonation flask fitted with a reflux condenser, thermometer and stirrer. After adding 50 ml of water and 12 g of calcium hydroxide the mixture is stirred at reflux temperature for 4 hours. The solvent is subsequently removed on a rotary evaporator and the residue is taken up in 600 ml of methyl acetate. The suspension obtained is stirred at room temperature for 1 hour. The solid is then filtered off under suction and rinsed with 300 ml of methyl acetate. The filtrate is concentrated completely on a rotary evaporator and there are obtained 18.1 g of a residue with 5.1% tocopherols (tocopherols+tocotrienols) (86% yield).

EXAMPLE 5

A tocopherol concentrate of the following composition is used as the starting material:

|  | Wt. % |
|---|---|
| Tocopherols | 19.5 |
| Fatty acids | 38 |
| Fatty acid esters | 2 |
| Glycerides | 2 |

| -continued | |
|---|---|
| | Wt. % |
| Residue | 38.5 |

100 g of the above concentrate are taken up in 750 ml of isopropanol while gassing with argon in a four-necked sulfonation flask filled with a reflux condenser, thermometer and stirrer. After adding 50 ml of water and 12.5 g of calcium hydroxide the mixture is stirred at reflux temperature for 4 hours. The solvent and the water are subsequently removed on a rotary evaporator and the residue is taken up in 750 ml of methyl acetate. The suspension obtained is stirred at room temperature for 1 hour. The solid is then filtered off under suction and rinsed with 100 ml of methyl acetate. The filtrate is concentrated completely on a rotary evaporator and there are obtained 49.5 g of a residue with 37.9% tocopherols (96% yield).

I claim:

1. A process for concentrating naturally occurring ingredients in a material derived from natural sources wherein said natural occurring ingredients are selected from the group consisting of natural occurring tocopherols, steroids or mixtures thereof comprising treating said material with calcium hydroxide in a solvent medium containing water and a water-miscible inert organic solvent to form calcium salts of the fatty acids present in said material, removing the water miscible organic solvent from said treated material, thereafter adding a water-immiscible polar solvent to precipitate these calcium salts and removing said calcium salts to leave a residue containing the natural occurring ingredients.

2. The process of claim 1 wherein said material is derived from a vegetable oil or fat.

3. The process of claim 2 wherein said material is derived from sunflower oil, soya oil, rape oil, cotton seed oil or palm oil.

4. The process of claim 3 wherein said material contains fatty acids and glyceride esters of fatty acids in addition to said ingredient.

5. The process of claim 2 wherein said organic solvent is a lower alcohol with 1-6 carbon atoms.

6. The process of claim 5 wherein the solvent medium contains from about 3 to about 15 wt. % of water based on weight of the solvent medium.

7. The process of claim 6 wherein said material is treated with calcium hydroxide at a temperature of about 60° C. to about 110° C.

8. A process for concentrating natural occurring ingredients selected from the group consisting of natural occurring tocopherols, steroids and mixtures thereof in a material derived from a natural source containing in addition to said ingredients fatty acids and glyceride esters of fatty acids comprising treating said material with calcium hydroxide in a solvent medium containing water and water-miscible inert organic solvent to form calcium salts of said fatty acids, precipitating said thus-formed calcium salts after first removing said water-miscible solvent, said precipitation being carried out by the addition of a water immiscible polar solvent, removing said precipitate from said treated material to produce in said treated material a concentration of said ingredients of from about two to about six times the weight percent of that weight percent of said ingredients in the naturally derived material prior to treatment with calcium hydroxide.

9. The process of claim 8 wherein said material is derived from vegetable oils or fats.

10. The process of claim 9 wherein said material is derived from sunflower oil, soya oil, rape oil, cotton seed oil or palm oil.

11. The process of claim 10 where said organic solvent is a lower alcohol containing from 1 to 6 carbon atoms.

12. The process of claim 11 wherein the solvent medium contains from about 3 to 15 wt. % of water based upon the weight of the solvent medium.

13. The process of claim 12 wherein said material is treated with calcium hydroxide at a temperature of from 60° C. to about 110° C.

* * * * *